(12) United States Patent
Bankers et al.

(10) Patent No.: US 7,793,861 B2
(45) Date of Patent: *Sep. 14, 2010

(54) PISTON ACTUATED VAPOR-DISPERSING DEVICE

(75) Inventors: Jeffrey Bankers, Phoenix, AZ (US); Kevin Hafer, Phoenix, AZ (US)

(73) Assignee: The Dial Corporation, Scottsdale, AZ (US)

( * ) Notice: Subject to any disclaimer, the term of this patent is extended or adjusted under 35 U.S.C. 154(b) by 662 days.

This patent is subject to a terminal disclaimer.

(21) Appl. No.: 11/654,464

(22) Filed: Jan. 17, 2007

(65) Prior Publication Data

US 2008/0169354 A1    Jul. 17, 2008

(51) Int. Cl.
| | |
|---|---|
| A24F 25/00 | (2006.01) |
| A61L 9/04 | (2006.01) |
| B67D 7/08 | (2010.01) |
| B67D 7/00 | (2010.01) |
| B05B 1/08 | (2006.01) |
| B05B 9/00 | (2006.01) |
| A62C 13/62 | (2006.01) |
| B65D 69/00 | (2006.01) |
| B65D 85/00 | (2006.01) |
| B67B 7/00 | (2006.01) |
| B65B 53/00 | (2006.01) |

(52) U.S. Cl. ............................ 239/50; 239/6; 239/44; 239/72; 239/73; 239/102.1; 239/102.2; 239/51.5; 239/56; 239/302; 239/326; 206/223; 206/525; 222/1; 222/3; 428/34.9

(58) Field of Classification Search ............ 239/44, 239/6, 72, 73, 102.1, 102.2, 274, 47, 51.5, 239/57, 145, 302, 326, 70, 68, 69, 45, 50, 239/56; 206/223, 525; 222/1, 3; 428/34.9
See application file for complete search history.

(56) References Cited

U.S. PATENT DOCUMENTS

| | | | | |
|---|---|---|---|---|
| 2,608,436 | A | * | 8/1952 | Baughman .................. 239/47 |
| 4,059,227 | A | * | 11/1977 | Hunter ........................ 239/1 |
| 4,477,414 | A | | 10/1984 | Muramoto et al. |
| 4,869,407 | A | | 9/1989 | Booth, Jr. et al. |
| 4,946,100 | A | * | 8/1990 | Flemming et al. ............. 239/1 |
| 5,221,025 | A | * | 6/1993 | Privas .......................... 222/1 |
| 5,447,273 | A | * | 9/1995 | Wozniak ..................... 239/70 |
| 5,449,117 | A | * | 9/1995 | Muderlak et al. ............. 239/6 |
| 5,515,842 | A | * | 5/1996 | Ramseyer et al. ...... 128/200.18 |
| 5,776,561 | A | | 7/1998 | Lindauer |
| 5,954,268 | A | | 9/1999 | Joshi et al. |
| 5,970,974 | A | * | 10/1999 | Van Der Linden et al. ................... 128/200.16 |
| 6,223,746 | B1 | * | 5/2001 | Jewett et al. ........... 128/203.12 |
| 6,264,548 | B1 | * | 7/2001 | Payne et al. ................. 454/157 |
| 6,267,297 | B1 | * | 7/2001 | Contadini et al. ............. 239/1 |
| 6,595,208 | B1 | * | 7/2003 | Coffee et al. .......... 128/203.12 |

(Continued)

*Primary Examiner*—Len Tran
*Assistant Examiner*—Steven M Cernoch
(74) *Attorney, Agent, or Firm*—Paul A. Pappalardo

(57) ABSTRACT

A vapor-dispersing device comprising a moveable piston with an evaporative member is described that operates by the repetitive movement of the piston to bring the evaporative member into repeated contact with the exposed end of a liquid transfer means to wick volatile liquid out from a reservoir onto the evaporative member and to expel vapors out through vents.

21 Claims, 9 Drawing Sheets

U.S. PATENT DOCUMENTS

| | | | |
|---|---|---|---|
| 6,655,604 B2 * | 12/2003 | Tuttobene, Jr. | 239/6 |
| 6,827,286 B2 * | 12/2004 | Zobele | 239/44 |
| 6,923,383 B1 | 8/2005 | Joshi et al. | |
| 2003/0235522 A1 | 12/2003 | Harrop et al. | |
| 2004/0021001 A1 * | 2/2004 | Zobele | 239/44 |
| 2006/0261179 A1 * | 11/2006 | Davies et al. | 239/34 |

* cited by examiner

PISTON ACTUATED VAPOR-DISPERSING DEVICE

FIELD OF INVENTION

The present invention relates to electromechanical vapor-dispersing devices and in particular to a vapor-dispersing device with a moveable piston that repeatedly brings an evaporative member such as a porous pad into contact with the end of a liquid transfer means placed within a reservoir and in communication with a volatile liquid. Upon contact with the liquid transfer means, the evaporative member draws up the liquid from the reservoir and moves air around via a bellows effect that evaporates the volatile liquid from the device into the adjacent environment in a linear and controlled manner.

BACKGROUND

Vapor-dispersing devices are well known and include a variety of devices for vaporizing a liquid such as a perfume or insecticide into the surrounding environment. For example, vapor-dispersing devices include electrical devices with resistive heater modules and/or fans for driving liquids into the vapor phase, passive devices that rely on pads, wicks, or combinations thereof having large surface area for evaporating liquids without energy input, and simple aerosol sprays that propel and disperse liquids into fine droplets that evaporate in the air. Vapor-dispersing devices that are electrically powered are very common in home and institutional settings around the world. These devices may comprise a bottle of volatile liquid and they may operate by heat to volatize the liquid. Most common of these devices are air fresheners wherein a porous plastic wick is in communication with a bottle of scented fragrance oil and wherein the wick, operating as both a liquid transfer means and evaporative member and is continuously saturated with the fragrance, is placed in close proximity to a resistive heater element that accelerates the evaporation of the liquid from the wick. Another common configuration for a household air freshener comprises a bottle of scented fragrance oil with a porous plastic wick positioned in front of a fan. In these devices the fan moves air across the wick and the scented air is expelled into the immediate environment. These devices exist in the marketplace, both house current powered (110 v/220 v, AC) and battery powered (1.5 v, 3 v, 9 v, etc., DC). Exemplary devices include the Glade® Plugins® Scented Oil and Plugins® Scented Oil Fan air freshener products from S.C. Johnson & Son, Inc., and the Mobil'Air® Portable Electric Diffuser air freshener from Reckitt Benckiser. More elaborate products include piezoelectric devices wherein the scented fragrance oil is wicked up from a reservoir onto a vibrating plate where it is expelled into very fine droplets that quickly evaporate. One such device is the battery operated Glade® Wisp® Scented Oil Fragrancer air freshener from S.C. Johnson & Son.

In spite of the fact that fan, heater, fan plus heater, and piezoelectric air fresheners have dominated the marketplace over the last decade or so, there remain many limitations to such electronic devices. Most problems relate to the fact that the wick is both the evaporation medium and the liquid transfer means and as the evaporation surface it either needs to be of a huge size (e.g., a thick fiber bundle) or heated by a proximate heating element. Invariably these devices slow down since the porous wicks clog with the less volatile ingredients and the spectrum of fragrance notes changes throughout the lifetime of the device, particularly if the wick is comprised of a fiber bundle and used in association with an aqueous fragrance solution containing a surfactant. In that instance, the large fiber wick will clog over time with the non-volatile surfactants and emulsifiers used to stabilize in the fragrance solution. In the heated example, the saturated heated wick continually leaves behind dark yellow, non-volatile base notes, and the wick clogs with no further new surfaces and unclogged pores left to assist in evaporation.

We have invented a unique way to circumvent these limitations by using a liquid transfer member and a moving evaporative member that are kept from constant contact with one another, and wherein the evaporative member is kept from complete saturation so that a continuous fresh surface is available for evaporation of volatile liquid. The way the present invention accomplishes this is by having a moveable piston that moves the evaporative member repeatedly into momentary contact with the end of the liquid transfer means with each stroke. By moving the evaporative surface and keeping it from full saturation, the evaporation of the liquid is more controlled and the distribution of the volatile components remains more constant throughout the evaporation of the liquid. The movement of the piston also serves as a bellow-means to expel the air treated with the volatile material and still residing in the device out into the environment.

Vapor-dispersing devices that contain pistons are extremely scant in the literature and are all based on movement of a piston to increase internal pressure within a reservoir to push liquid out. For example, U.S. Pat. No. 5,954,268 to Joshi, et al. and U.S. Pat. No. 5,776,561 to Lindauer both describe reservoirs that may be pressurized by depression of a piston and wherein the pressure forces liquid fragrance up a capillary tube and out onto an evaporative surface formed in the shape of a decorative flower.

U.S. Pat. No. 4,477,414 to Muramoto, et al. describes a piston operable device where depression of the piston forces liquid out through a capillary tube and onto an impregnation member where it evaporates. U.S. Pat. No. 6,923,383 to Joshi, et al. describes a device wherein a piston-actuated pressurization expels liquid through a restrictive opening. Lastly, piston actuated spray devices include the device described in U.S. Pat. No. 5,221,025 to Privas.

Devices that employ a bellows-type action to expel scented air include the devices described in U.S. Pat. No. 4,869,407 to Booth, et al.

None of these devices employ a moveable piston in a non-pressurized device for effecting the repeated touching of an evaporative member onto the end of a liquid transfer means such that volatile liquid is pulled from a reservoir and evaporated into the adjacent environment in a controlled manner.

SUMMARY OF THE INVENTION

It has now been discovered that placing the evaporative member in motion to repeatedly touch the end of a liquid transfer means in communication with a volatile liquid is a unique and effective way to smooth out delivery of the volatile liquid over time.

For example, the present invention relates to a device that minimally comprises a housing with a vent for air exchange, a movable piston with an attached evaporative member such as a flat porous pad, a reservoir containing a volatile liquid, a liquid transfer means in communication with the liquid, an electromechanical means to move the piston, a drive means connecting the piston with the electromechanical means, and an electrical means to power and control the electromechanical means and hence the piston, embodiments of which are encompassed in the following drawing figures. The invention provides a previously unheard of method for evaporating a liquid that involves repetitive touching of an evaporative member onto the end of a liquid transfer means to convey volatile liquid from a reservoir to the evaporative member where it may evaporate into the surrounding environment.

DETAILED DESCRIPTION OF THE INVENTION

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function, the size, and arrangement of the elements described without departing from the scope of the invention as set forth in the appended claims. Most importantly, changes in shape and size of the overall device do not depart from the intended scope of the invention.

That said, the present invention relates to a piston-actuated electromechanical vapor-dispersing device that shows a more linear evaporation of volatile liquid than conventional electrical devices utilizing heater and/or fan elements or passive devices with large cotton or fiber wicks.

The present invention relates to a device that minimally comprises a housing with an air vent, a movable piston with an evaporative member, a reservoir with an opening containing a volatile liquid, a liquid transfer means in communication with said volatile liquid, an electromechanical means and drive means to move the piston in repetitive strokes, and an electrical means to power and control the electromechanical means and hence the piston. In the simplest embodiment, the piston moves in a stroke range somewhere between the confines of an extreme first position where the evaporative member on the piston has touched onto the end of the liquid transfer means, to an extreme second position where the evaporative member is out of contact (i.e. detached) from the liquid transfer means and is as far away from the liquid transfer means as the electromechanical and drive means and the housing length will allow. Between these two extreme positions, the piston moves along a path within a housing to bring the evaporative member repeatedly into contact with the end of the liquid transfer means and past at least one vent, and to provide air movement into the device, around the evaporative member and out to the environment to effectively evaporate the liquid. The repeated stroke of the piston provides a bellows effect that facilitates movement of air within the device and movement of vapor from the interior of the device to the surrounding environment. More linear transfer of liquid to vapor is possible over conventional devices because the evaporative member can be kept from complete saturation.

Figure 1:
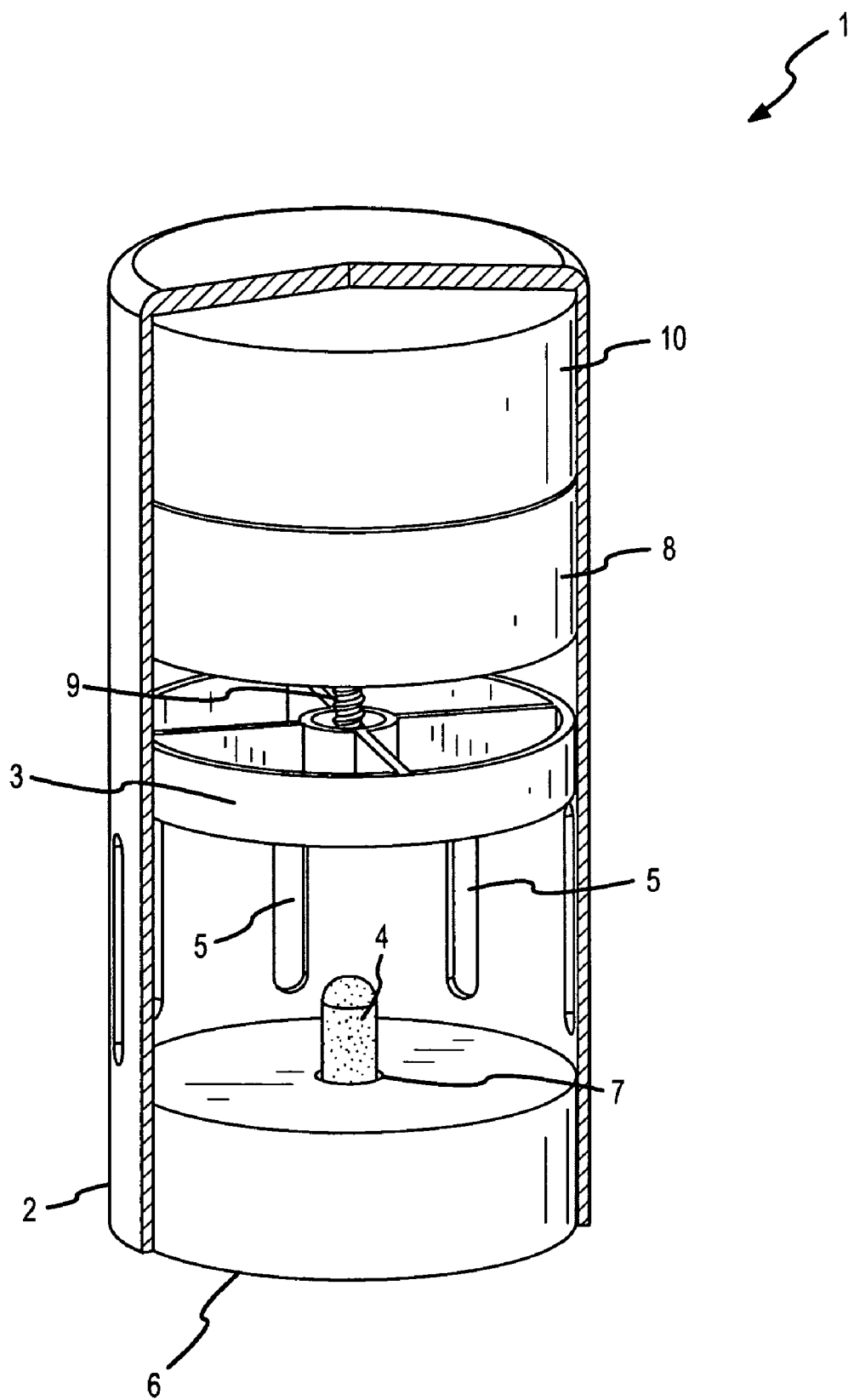
FIG. 1 conceptually outlines one embodiment of the vapor-dispersing device of the present invention with the movable piston in a one position.

Referring now to FIG. 1, one embodiment of the vapor-dispersing device 1 of the present invention comprises housing 2, moveable piston 3, liquid transfer means 4, air vent 5, reservoir 6, opening 7, electromechanical means 8, drive means 9, and electrical control means 10. The size of the overall device 1 may be any size practical to maintain function and portability. It may be miniaturized, just a few inches in height and width, or the device may be quite large, as large as 12 inches or more in height and in width. A smaller dimensioned device may be used to treat a small room with volatized material such as an insecticide or fragrance, whereas a large unit may be used in institutional and industrial settings to disperse large amounts of vaporized material into much larger spaces including outdoor areas. The device 1 may sit on a surface, such as a floor, table or a shelf in a home or office, or it may be mounted to a wall or to a ceiling or plugged directly into an electrical outlet for support. It may be placed out of sight, for example inside of HVAC air ductwork, or it may be placed outdoors. It may be decorative and displayable or it may be utilitarian in appearance and hidden from view when in use. Depending on the configuration of the individual elements and the nature of the volatile liquid, the device need not be operated in a vertical and upright position with the reservoir at the bottom end of the device. Some embodiments of the present invention may be operated in a position completely upside down from that shown in FIG. 1, lying down, or in any other position for that matter.

The housing 2 defines the overall shape of the device 1. The housing may be comprised of any suitable material such as metal, plastic, glass or fiberboard, or combinations thereof. It may be cylindrical, cubic or rectangular in shape. Although any shape is theoretically possible, a cylindrical shape is preferred for simplicity of fitting a moveable piston inside (explained below). A preferred embodiment is to have a molded plastic or fiberboard cylinder, i.e. a tube, defining the sidewalls of the housing, with other components (detailed below) pressed into each end of the housing to close off both top and bottom ends. Overall, the housing 2 is a container with top, bottom and sidewalls that define an interior space. Most preferred is a cylinder shaped housing 2 with dimensions of from about 1.5 to about 8 inches in height and from about 0.5 to about 4 inches in diameter.

Also depicted in the embodiment of FIG. 1 is the vent 5 on the housing 2. It must be stressed that the size, shape, and number of vents is entirely variable. There may be one vent 5, or there may be many in the housing. The number and size of the vents are chosen such that the rate of evaporation of the volatile liquid within the device conforms to the application and the consumer needs. For example, if the device 1 is embodied as an air freshener, the vents on the device may be designed such that the supply of fragrance inside is evaporated to the environment in a reasonable time such as over a 30-90 day period. If the device is embodied as an insecticide disperser, then the vents in the device may be designed for another rate of delivery of the volatile liquid or fashioned to allow passageways for insects to move in and out of the device. The vent or vents 5 on the housing are essentially "holes" that allow the exchange of air between the inside and outside of the housing. The device is designed to transfer liquid from the inside of the device to vapor in the environment outside of the device, and thus the vent or vents are what make the movement of vapor to the outside of the device possible. Ideally the vent or vents are sized such that a child's finger cannot be inserted through it or them, for example smaller than 0.5 inches in diameter if round and unguarded. Otherwise the vent or vents may be screened in with mesh (plastic, metal, etc.), or an entire section of the housing may be constructed of mesh or screen and this grill area becomes the vent or vents. The vent or vents are positioned on the housing such that the movement of the piston within the housing moves air through them. The vent 5 may include adjustment means, such as moveable louvers or windows that allow control over the size of the openings in the device. One such embodiment may be to have concentric cylindrical tubes as the housing whereby rotation of the outer tube in relation to the inner tube opens and closes the vents 5. The vent or vents 5 may add to the overall décor of the device and can take on any decorative shape and arrangement for this purpose. Similarly any screening over the vents may be decorative or utilitarian.

Continuing with FIG. 1, an additional essential element of the present invention is a moveable piston 3 within the housing 2. The moveable piston is dimensioned to fit the interior of the housing such that there is little resistance to movement along the interior length of the housing and a reasonably close fit to the interior walls of the housing such that the piston may pull in ambient air and push out vapors through the vent or vents described above with each stroke. The piston necessarily comprises a top and bottom, along with sidewalls, wherein the sidewalls define the thickness between the top and bottom. The most preferred configuration for the moveable piston is disc-shaped such that it may fit the preferred cylindrical shape for the housing, and in this particular embodiment the piston would comprise a top and bottom and a sidewall having a circumference that reasonably matches the inside circumference of the housing. If a rectangular or square shaped housing were utilized, then the moveable piston would necessarily be configured to a rectangular or square shape, respectively. The thickness of the piston (determined by the height of the sidewalls mentioned) may be varied, but for practical and cost reasons the height/thickness is preferentially from about 0.125 inches to about 2 inches. The most preferred dimensions for a disc-shaped piston is a diameter of from about 0.5 to about 4 inches and a height/thickness of from about 0.25 to about 1 inch. The preferred material of construction for the moveable piston 3 is injection molded or thermoformed plastic, although other materials such as wood, metal, porous plastic, ceramic or fiberboard, or combinations of any of these materials are within the scope of the present invention. The piston may be constructed of one continuous part or it may be an assembly of more than one part, wherein the parts are glued or welded together. Most preferred is to utilize an injection molded, disc-shaped plastic piston having a recess molded in or post-drilled into either the top or bottom of the piston. It is preferred that either the top or the bottom of the piston comprises a relatively planar configuration such that a flat evaporative member may be attached to it (explained below). A preferred embodiment for the piston comprises a molded plastic wheel shape with spokes. As described below, once the evaporative member is in place on the piston, a solid surface (i.e., a faceplate) is provided on the piston to ensure that the piston can move air when in motion.

Figure 7:
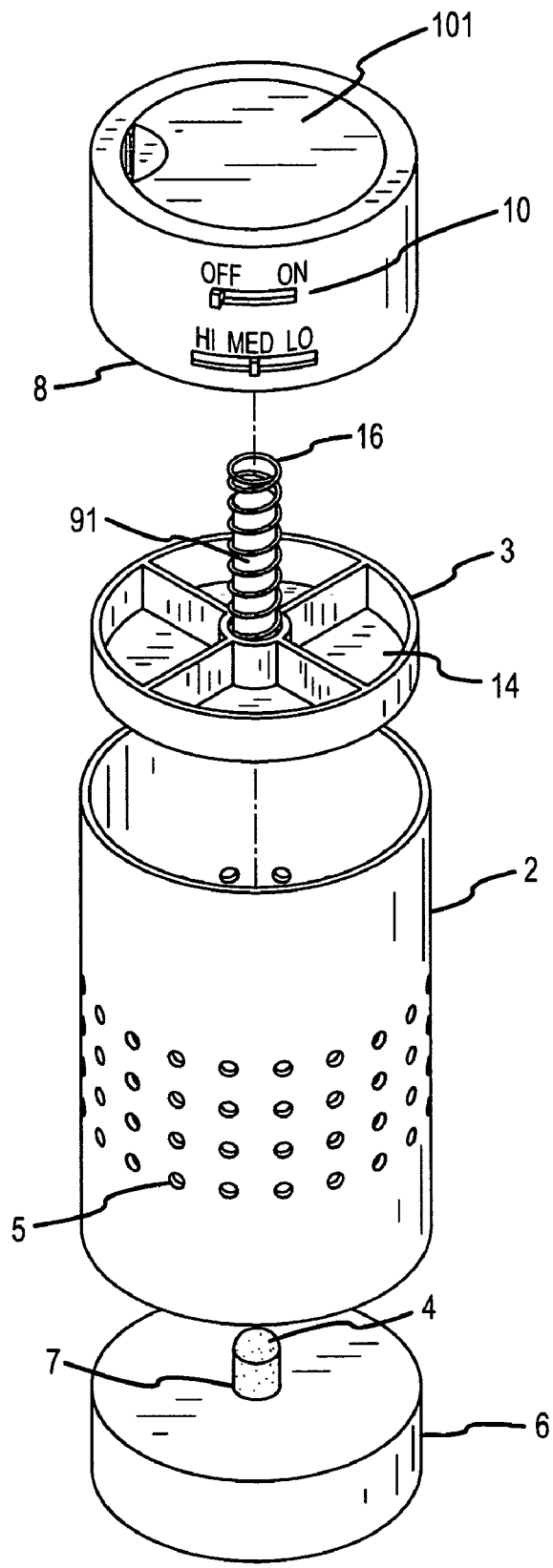
FIG. 7 shows an exploded view of one embodiment of the vapor-dispersing device of the present invention.
Figure 10:
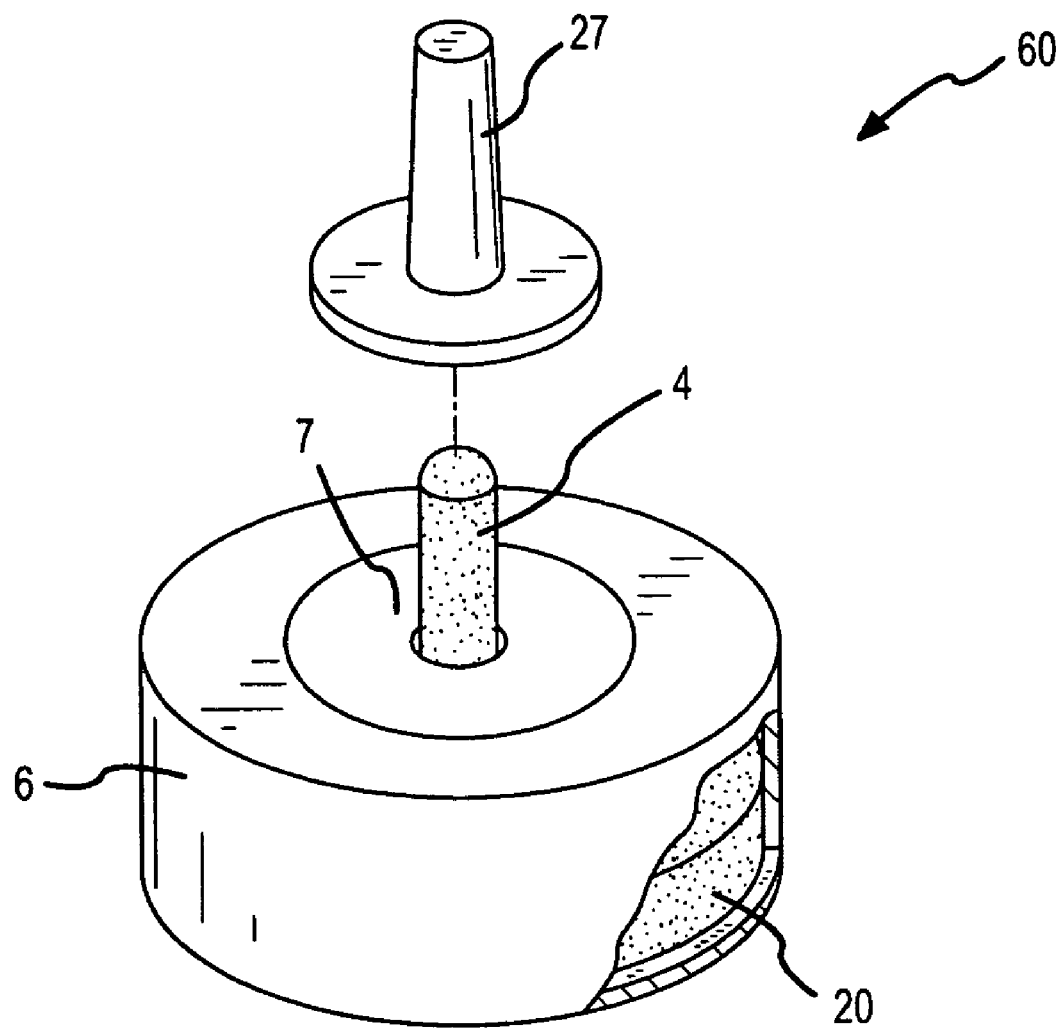
FIG. 10 shows one embodiment of an article of manufacture that provided for a refill reservoir for use in the vapor-dispersing device of the present invention.

Still referring to FIG. 1 (and also to FIG. 10 for clarity), another essential element of the vapor-dispersing device of the present invention is the reservoir 6, containing the volatile liquid and having an opening 7 to accept the liquid transfer means, wherein the reservoir is positioned at one end of the housing 2 and in the stroke path of the moveable piston 3. The reservoir 6 is dimensioned and constructed of materials suitable to hold the volatile liquid to be vaporized from the device. The preferred capacity of the reservoir is from about 1 to about 500 milliliters, and the reservoir is necessarily a container having top, bottom, sides and an interior volume. The preferred shape of the reservoir is disc shaped, with dimensions of from about 0.5 inches in diameter to about 4 inches in diameter and from about 0.5 inches in height to about 3 inches in height. The important factor to the size and shape of the reservoir 6 is that it fit within one end of the housing 2. Thus if the housing is cylindrical, then the preferred shape of the reservoir may be disc-shaped, however any shape reservoir is within the scope of the invention. As mentioned above, a convenient configuration for these components, and one that simplifies assembly of the device is to use a fiberboard, metal or plastic tube for the housing 2 and to press-fit a disc-shaped reservoir 6 into one end of the tube such that the bottom of the reservoir becomes the bottom of the housing and the bottom of the device itself. Such a configuration also allows for the reservoir 6 to be removable and replaceable by the user. As illustrated in FIGS. 7 and 10, and described in more detail below, the preferred configuration is for the reservoir 6, (containing the volatile liquid, liquid transfer means and a sealing member for shipping and storage), to be merchandised as a refill for the device of the present invention and for the user to place it within the housing. Placement of the reservoir into the housing will necessarily place the liquid transfer means of the reservoir into intermittent contact with the evaporative member on the moving piston.

The preferred materials of construction for the reservoir 6 are polyethylene, polypropylene, polyvinyl chloride (PVC), glass, or metal, with the material chosen on the basis of cost, manufacturability and compatibility with the volatile material. Injection molding, blow-molding or thermoforming processes may be used to form the reservoir. The reservoir may be one-piece blow-molded, injection-molded, or simple molded construction or may be two or more pieces that are assembled together make the complete reservoir. For example, the reservoir may be comprised of a small disc-shaped container with sidewalls and a bottom defining a capacity of from about 1 mL to about 500 mL, having a separate lid that may be snapped, glued or sonically welded onto the sidewalls of the container to complete the reservoir. The reservoir necessarily has a top, a bottom and sides defining an interior capacity, an opening, and as mentioned above is preferentially disc-shaped.

The opening 7 is configured on one face of the reservoir 6. The opening may be created from the blow-pin used in a plastic blow molding operation, or it may be molded into a glass reservoir, or molded into an injection molded top cover of the reservoir or drilled in during a later operation. This opening is preferably a small round hole, but regardless of the shape it should be complementary to the shape of the liquid transfer means that will be fitted through it. Optionally there may be a rubber or plastic fitment fitted within the opening of the reservoir to help provide a seal around the inserted liquid transfer means. In the instance of a fitment, the liquid transfer means is pressed into the inner hole of the fitment and the fitment/liquid transfer means subassembly is pressed in the opening of the reservoir. When the liquid transfer means 4 is preferably a capillary or a rod-shaped means, the opening 7 on the reservoir 6 may preferably be round. To complement the preferred sizes/shapes of the liquid transfer means 4, the opening 7 may be from about 0.03125 to about 1 inch in diameter (if round to accommodate a capillary or rod shaped liquid transfer means) or about this general size if the opening is configured to some other shape such as square, rectangular or triangular. Regardless of the shape of the opening 7 on the reservoir, it is expected that the opening will take up from about 0.0001 to about 1 square inch of surface area and will accommodate the liquid transfer means or a subassembly comprised of the liquid transfer means and a suitable fitment.

Also essential to the present invention and depicted in FIG. 1 is the liquid transfer means 4. As described above, the liquid transfer means 4 is preferentially press-fit into the opening 7 of the reservoir 6, either with or without a fitment, and positioned such that one end is to the bottom of the reservoir to ensure complete transfer of the liquid contents out to the environment. The liquid transfer means may be as simple as a capillary tube, for example made from glass, plastic or metal and having a diameter of from about 1/64 to about 1/16 of an inch and having a first end and a second end separated by the length of the tube. The length of the liquid transfer means should be long enough to protrude out from the reservoir such that one end is reachable by the moving piston of the device. For example, the liquid transfer means may be a capillary tube of length from about 0.25 inch to about 5 inches. However, the liquid transfer means can be any length so long as a first end is positioned within the reservoir and in contact with the volatile liquid and a second end is protruding at least somewhat from the reservoir. Most preferred is to utilize a fine capillary tube as the liquid transfer means (e.g., glass or plastic, 1/32 inch diameter) and to position it to the bottom of the reservoir and to extend it in length from the reservoir such that it protrudes by only about 1/8$^{th}$ to about 1/4 inch. The first end of the liquid transfer means may be configured such that it can drain the reservoir completely, for example having a chisel point end rather than a squared off end that would sit and seal against the bottom of the reservoir preventing liquid flow. Alternatively, the liquid transfer means may be constructed of a porous material such as porous plastic. A preferred liquid transfer means is a porous plastic wick similar to those found in household electric "plug-in" scented oil air fresheners. Such porous plastic materials are described in U.S. Patent Application Publication US2005/0191481 and the preferred porosities (pore size and void volumes) and sintered plastics are incorporated herein by reference. The liquid transfer means may also be comprised of cellulose or plastic fibers, ceramics, wood or graphite. The dimensions of a porous liquid transfer means may be from about 0.125 to about 1 inch in width and long enough to protrude at least somewhat from the reservoir. The porous wick as the liquid transfer means may be rod-shaped or rectangular (stick-shaped). Most preferred is a molded sintered porous plastic wick in a rod-shape having dimensions of from about 0.125 to about 0.5 inches in diameter and from about 0.25 to about 3 inches in length. Most preferred is to press-fit this rod-shaped molded porous plastic wick into the opening 7 of reservoir 6, or to further utilize a fitment to improve the seal between the liquid transfer means and the circumference of the opening of the reservoir. When the liquid transfer means of the invention is constructed of porous material rather than from a simple tube, there will of course be some evaporation from this means. Although a more effective transfer of liquid is through utilization of a capillary tube, transfer of liquid may be affected through use of a porous material as the liquid transfer means, or from a combination of a capillary tube and a porous wick. For example, a porous plastic wick with a capillary tube as its core may form a subassembly that may function as the liquid transfer means of the present invention.

Figure 2:
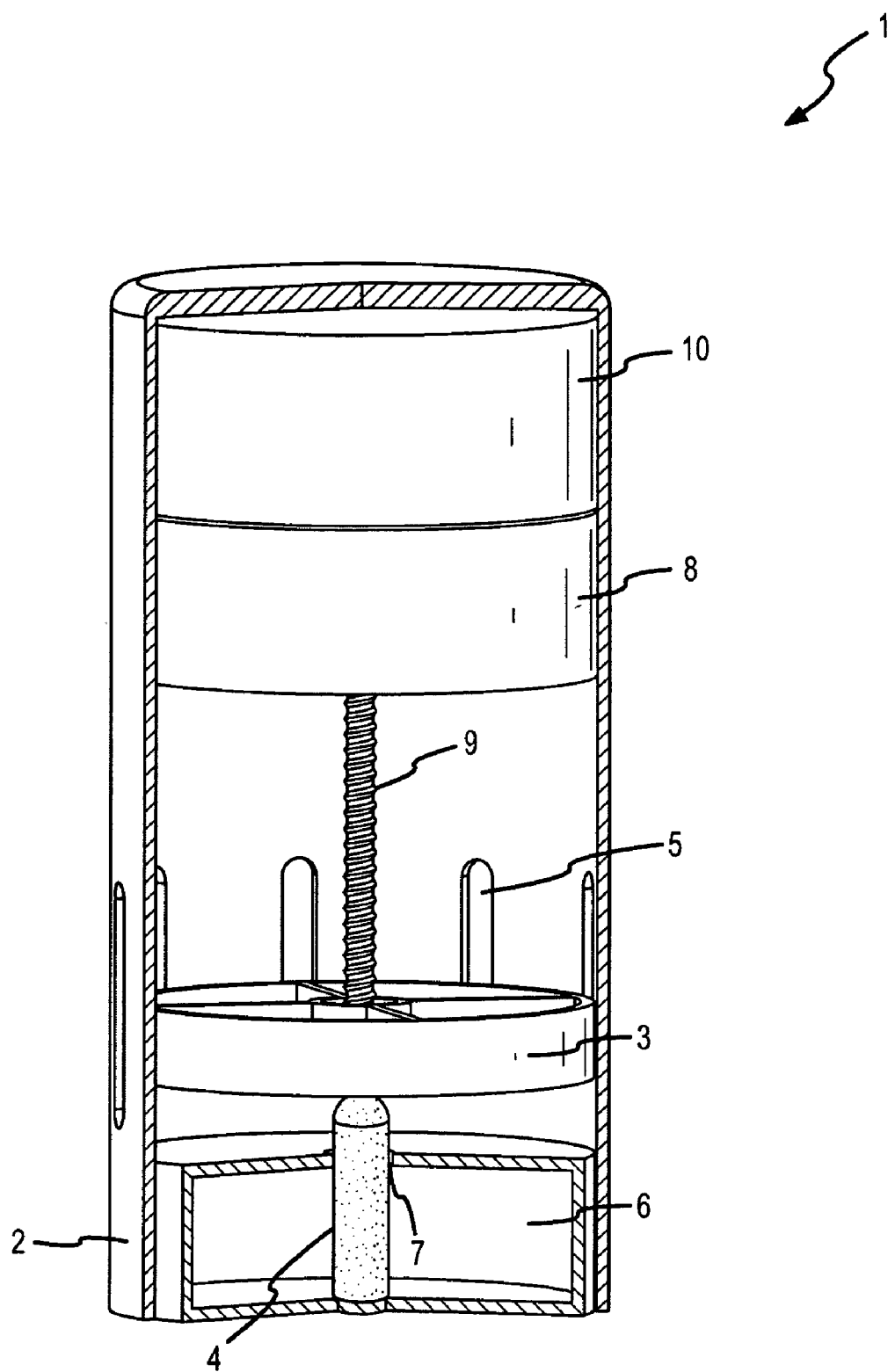
FIG. 2 conceptually outlines another embodiment of the vapor-dispersing device with moveable piston in a second position.
Figure 3:
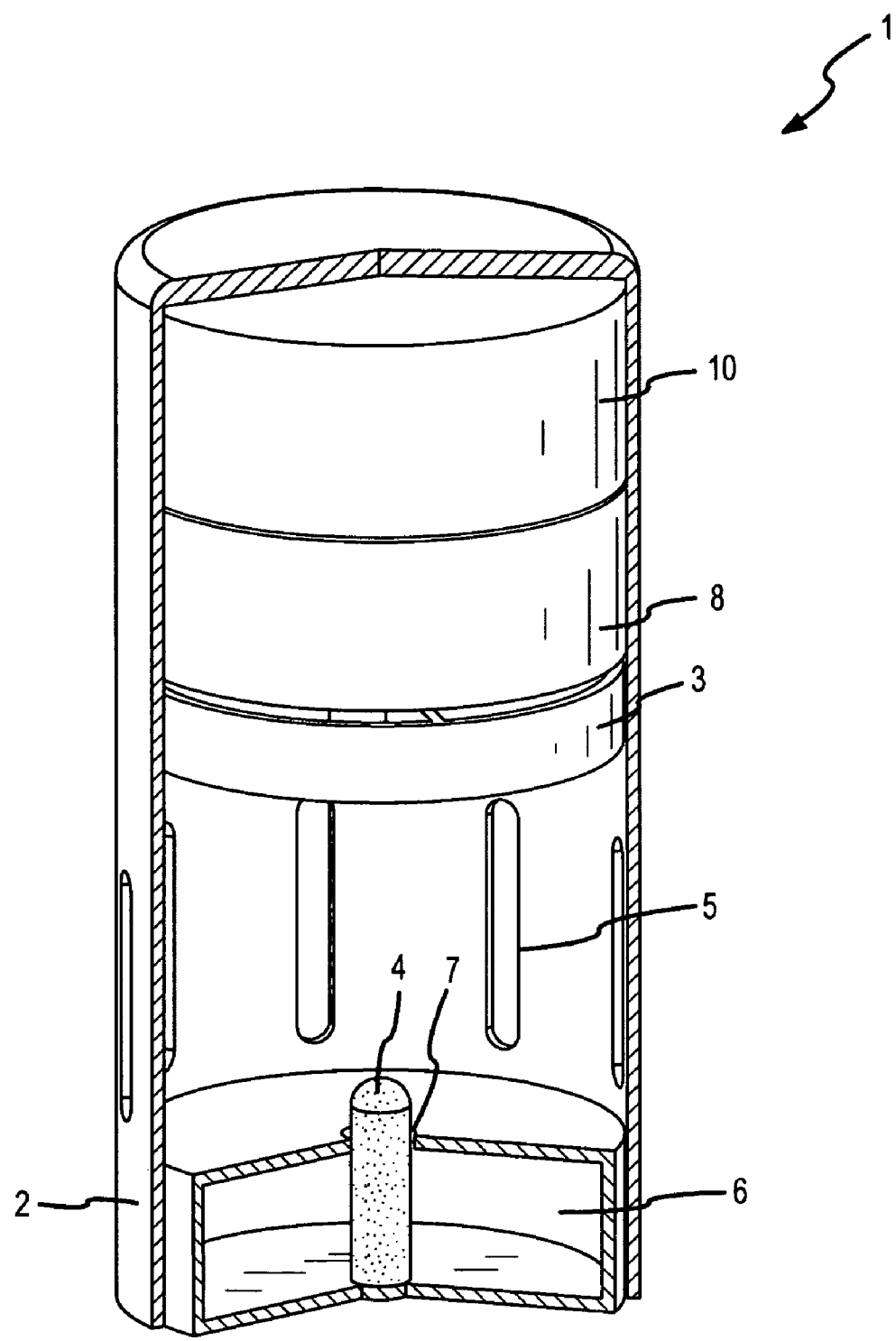
FIG. 3 conceptually outlines another embodiment of the vapor-dispersing device with moveable piston in a third position.

Referring now to FIGS. 2 and 3, one embodiment of the vapor-dispersing device of the present invention is shown with the piston 3 at each of two extreme first and second positions of a stroke length, respectively. FIG. 2 shows the moveable piston at an extreme first position wherein the piston 3 is in contact with the liquid transfer means 4 positioned in the opening 7 of the reservoir 6. FIG. 3 shows the moveable piston 3 at a second extreme position where the piston 3 is fully retracted away from any contact with the liquid transfer means 4. Essential to the working of the present invention is that the piston 3 move in a stroke length defined somewhere between these extreme first/lower and second/upper positions depicted in FIGS. 2 and 3 respectively, such that each stroke of the piston 3 operates to momentarily touch the liquid transfer means 4. Furthermore, each stroke of the piston 3 pulls air into and pushes air out through the vent(s) 5, whereby the piston functions as a bellows-means. The stroke of the piston 3 is the length measured between the first and second ends of the stroke, chosen somewhere between or equal to the extreme first and second positions of the piston shown in FIGS. 2 and 3. The chosen ends of the stroke length are where the piston stops and reverses direction. The stroke length may be determined in design and construction by the relative sizes of the parts, especially the drive means (described below), and/or may be automatically changed during operation of the device, or adjusted by the user. That being said, it is preferable to have a stroke length for the piston 3 from about 0.125 inches to about 7 inches and this stroke length may be permanently fixed or may be variable throughout the dispensing of the volatile liquid in the device.

The frequency of the piston stroking has a direct effect on the evaporation of the volatile liquid and may be set at a very wide range of frequencies. For example, the piston may move very rapidly, almost like a vibration, with short fast strokes possible though a solenoid arrangement or a rapid motor rotation. Or, in another embodiment, the piston may move very slowly with long slow strokes made possible by a motor and tooth-gear arrangement (described below). Depending upon the end-use, (air freshener, or insecticide), the size of the area to be treated, the amount of volatile liquid within the reservoir and how volatile the liquid is, the frequency of the piston strokes is preferably from about 1 stroke/hour to about 120 strokes/minute. The device may preferentially have a fixed stroke frequency or it may be changeable by the user or may be pre-programmed to change frequency throughout the dispensing of the volatile liquid. For example, the device may preferably change to a higher frequency toward the end of the contents of the reservoir to ensure evaporation of the last remaining volatile liquid in the device.

Figure 4:
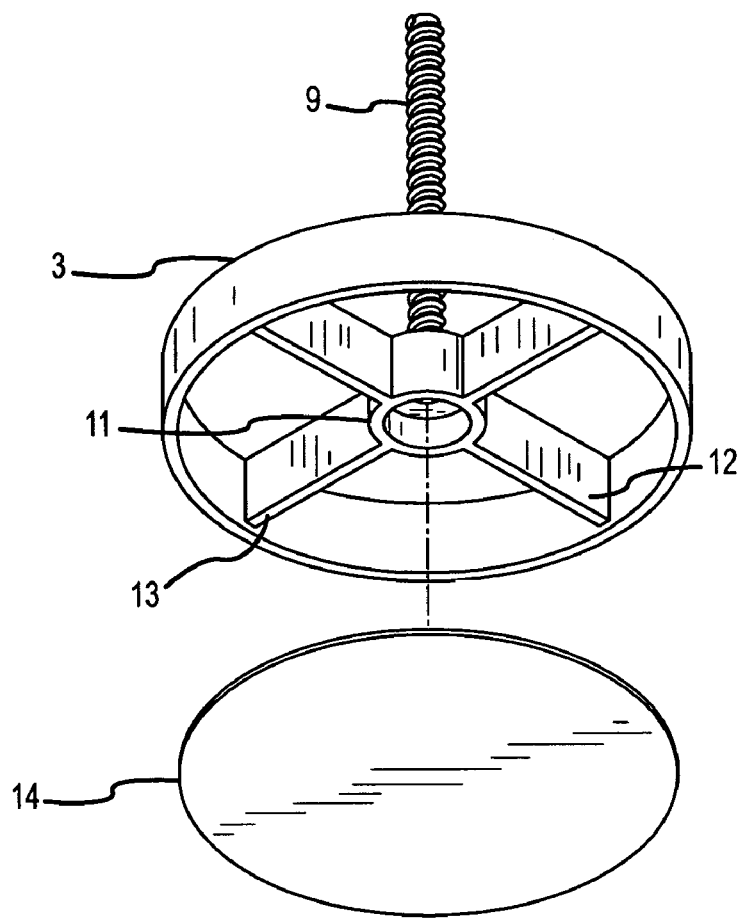
FIG. 4 shows an exploded view of one embodiment of the moveable piston of the vapor-dispersing device with evaporative member configured to fit on the piston.
Figure 5:
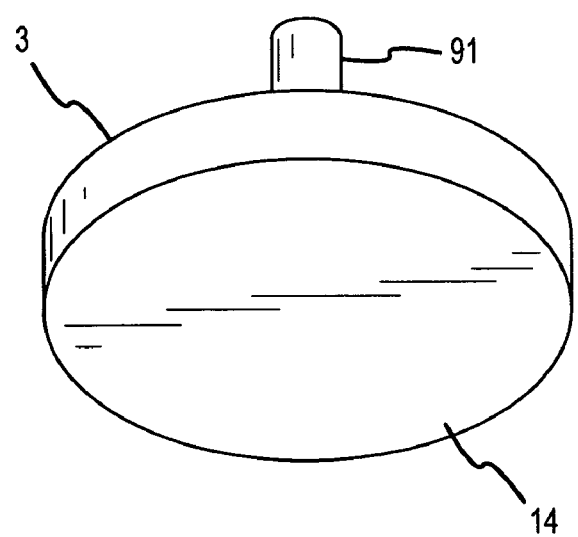
FIG. 5 shows another embodiment of the moveable piston of the vapor-dispersing device having a metal pin as the drive means and with evaporative member in place.

FIGS. 4 and 5 depict two preferred embodiments of the piston 3. As mentioned above and now shown in greater detail in FIG. 4, it is preferable to have an injection molded disc-shaped plastic part as the piston 3 in the present invention. It is preferred that the piston 3 further comprises a recess or hole 11 molded in or post-drilled into either the top or the bottom to accommodate the drive means 9. Furthermore, the piston 3 preferably has support ribs 12 each having edges 13 defining a recessed shelf. The support ribs may then be used to support the evaporative member 14 that will close off the spokes of the piston with a solid faceplate to ensure that it will move air during each stroke. When the evaporative member 14 is incorporated on the piston 3, the piston will necessarily have a closed off surface and will be able to move air. The piston with the evaporative member 14 will move the air upon each stroke since the evaporative member 14 will provide for the closed surface on the piston. Also shown in FIG. 4 is the drive means 9 that is used to connect the piston 3 to the electromechanical means (explained below). In this embodiment of the piston shown in FIG. 4, the drive means 9 is configured as a screw-gear, but it may also be a cam rod or a flat-toothed gear that will drive the piston. Drive means 9 may be pressed into a hole or appropriately shaped recess provided on either the top or bottom of the piston 3 (for example, a continuation of hole 11 through to the top of the part in FIG. 4 and thus not in view).

Referring again to FIG. 4, the evaporative member 14 is an essential component in the device of the present invention. The configuration of the evaporative member depends on the volatility of the liquid, the evaporation rate desired, the level of intensity of the vapor desired in the external environment around the device, and the application, (e.g., fragrance disperser or insecticide). The evaporative member may be any size, shape and thickness that can reasonably fit onto one side of the piston. It may be glued, press-fit, or melted on to the piston. Alternatively the evaporative member may be attached with fasteners such as Velcro® to allow for the user of the device to detach and replace the evaporative member. The preferred shape for the evaporative member 14 is disc-shaped to coincide with the preferred shape for the piston 3. The evaporative member may be any relatively flat absorptive material such as compressed cellulose (pulp), wood, graphite, ceramic, or porous plastic, or simply a pad of cotton, hair or loose synthetic fibers, or any combinations thereof. Most preferred is to construct the evaporative member 14 from $1/16$ to $1/2$ inch thick wet-laid pulp, for example AC-16 supplied by Filter Materials in a variety of thicknesses. This material is easily die-cut into discs and the scrap may be recycled into pulp so that there is no waste. Sheet stock of porous plastic, for example from $1/16$ to $1/2$ inch thick, may also be die-cut and used as the evaporative member except that the waste is not recyclable. In certain applications such as insecticide delivery, the pad may be pre-treated with other materials, for example even with adhesives for the added benefit of trapping insects. The piston 3 may be molded in the shape of a plastic wheel as shown in FIG. 4, with the ribs 12 forming the spokes and the central hole 11 forming the hub of the wheel, and that hub may then be used as the receptacle for the drive means 9. A disc-shaped evaporative member 14 as described above may be fixedly attached onto either the top or the bottom of the piston opposite to the side where the drive means 9 is attached, most preferably simply press fit into the recess provided by the ribs 13. Alternatively, the side of the evaporative member that is to be fixed to the piston may be cut with recesses (e.g., a "cross pattern") such that the evaporative member will securely press-fit over each of the spokes 12 of the piston 3. This is a preferred configuration when using a porous plastic disc as the evaporative member since it is a molded part and the recesses to fit around the spokes of the piston may be molded into the evaporative member rather than cut in.

FIG. 5 is another preferred embodiment of the piston 3, with drive means 91 comprised of the metal pin from a solenoid. It is preferred to have such a drive means pressed into a recess or hole provided for on the top or bottom of the piston as described above. Most preferred is to mold a single hole completely through the center of the plastic piston (such as the hub 11 above) such that the piston is symmetrical to reduce molding costs, and then to press fit the solenoid pin into that hole until it is securely seated.

Figure 6:
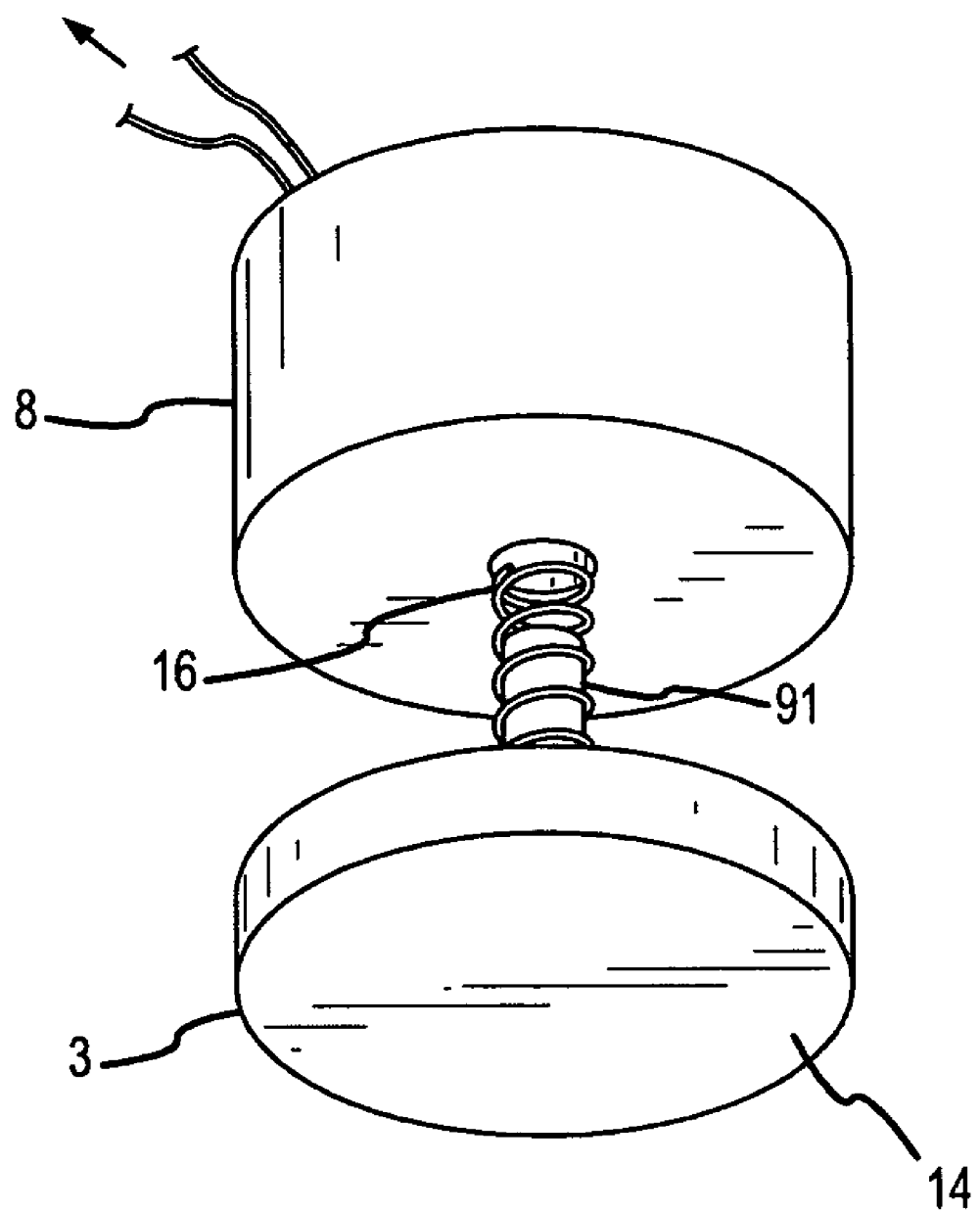
FIG. 6 shows a preferred embodiment of the electromechanical means, drive means and movable piston, wherein the electromechanical means together with the drive means comprise a solenoid, the metal solenoid pin and the solenoid return spring.

FIG. 6 details one configuration for a subassembly comprising the piston, the electromechanical means, and the drive means for incorporation into the device of the present invention. As mentioned above, one preferred embodiment is to move the piston with a solenoid, and for that preferred embodiment the drive means that connects the piston to the electromechanical means is preferably the metal pin of the solenoid and the electromechanical means is the remainder of the solenoid (the magnetic coil windings, housing, etc., less the pin). As shown in FIG. 6, piston 3 may be fitted with a solenoid pin 91. Fitted on the solenoid pin 91 is preferably the solenoid return spring 16. The solenoid 8, along with pin 91 and return spring 16, is designed to move piston 3 in repetitive strokes by intermittently powering the solenoid 8 with electrical control means 10. For example, electromechanical means 8 preferably comprises a pull-type solenoid that operates to pull up to its upper position upon supply of power to the solenoid. The piston then returns back down to a lower position at least partly in the reservoir by the force of the return spring 16 when the power is cut to the solenoid. Depending on the frequency of voltage pulses sent to the solenoid 8 from the electrical control means 10, the piston will move up and down to a particular frequency that is preferably from about 1 stroke per hour to about 120 strokes per minute. An audible "clicking" sound may emanate from the device of the present invention when configuring the device with a solenoid, and this sound may provide a unique audible cue to the consumer that the device is powered and working properly. A clicking noise when the device is in operation may be due to the metal pin hitting the inside of the solenoid body upon activation of the solenoid. The electric control means 10 may be comprised of a simple circuit to supply rectified DC voltage from an AC plug, and may feature an "on-off" switch (described below).

FIG. 7 delineates a preferred embodiment of the present invention in exploded view wherein the electromechanical means comprises a solenoid 8, the drive means comprises the metal pin 91 and return spring 16 of the solenoid, along with an electrical control means 10 further comprising on/off and "high/low" switches and a battery compartment door 101. For this preferred configuration of the device, the piston 3, in the preferred shape of a wheel, further comprises the evaporative member 14 attached to the bottom of the piston, and the solenoid pin 91 pressed into a central hub from the top of the piston. The preferred embodiment shown in FIG. 7 also features the preferred configuration for the housing 2, wherein the housing is comprised of a tube (that provides only the sidewalls of the device), the top of the electric control means 10 forming the top boundary of the housing, and the bottom of the reservoir 6 forming the bottom boundary of the housing, when these three parts are assembled together. This embodiment represents a very cost effective configuration for the device of the present invention, wherein the reservoir 6 and the electrical control means 10 are pressed into the top and bottom openings of a cylindrical tube 2 to form the overall shape and outer walls of the assembled device. Also shown in FIG. 7 is a liquid delivery means 4 pressed into the opening 7 of reservoir 6, and the vents 5 on the housing 2 configured as many small holes. In addition (and not shown) there may initially be a seal over the liquid delivery means 4 or over the entire reservoir 6 such that the device can be merchandised without fear of leakage from the reservoir. For example, a foil or shrink-wrap plastic film can cover the exposed end of the liquid delivery means or the entire reservoir when the device is merchandised.

Figure 8:
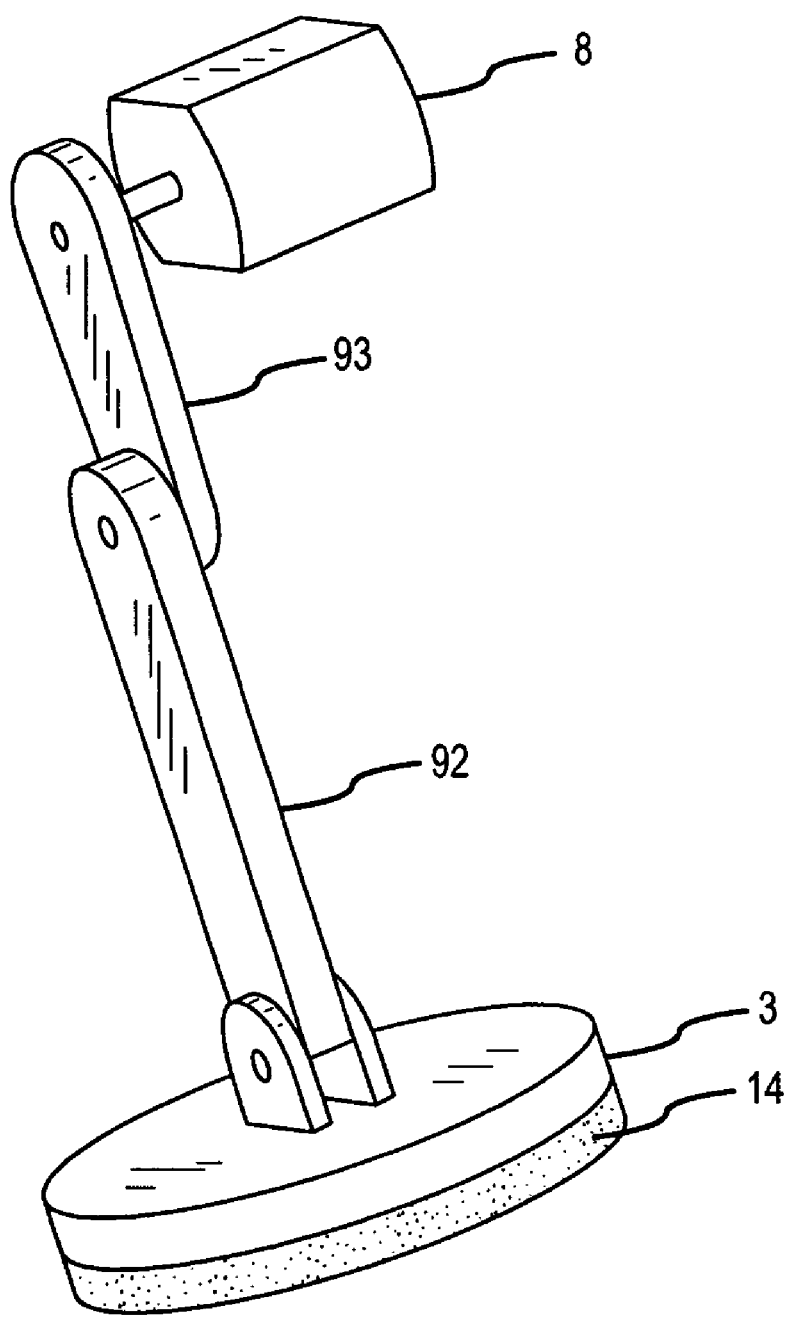
FIG. 8 shows one embodiment of the electromechanical means, the drive means and moveable piston of the vapor-dispersing device.
Figure 9:
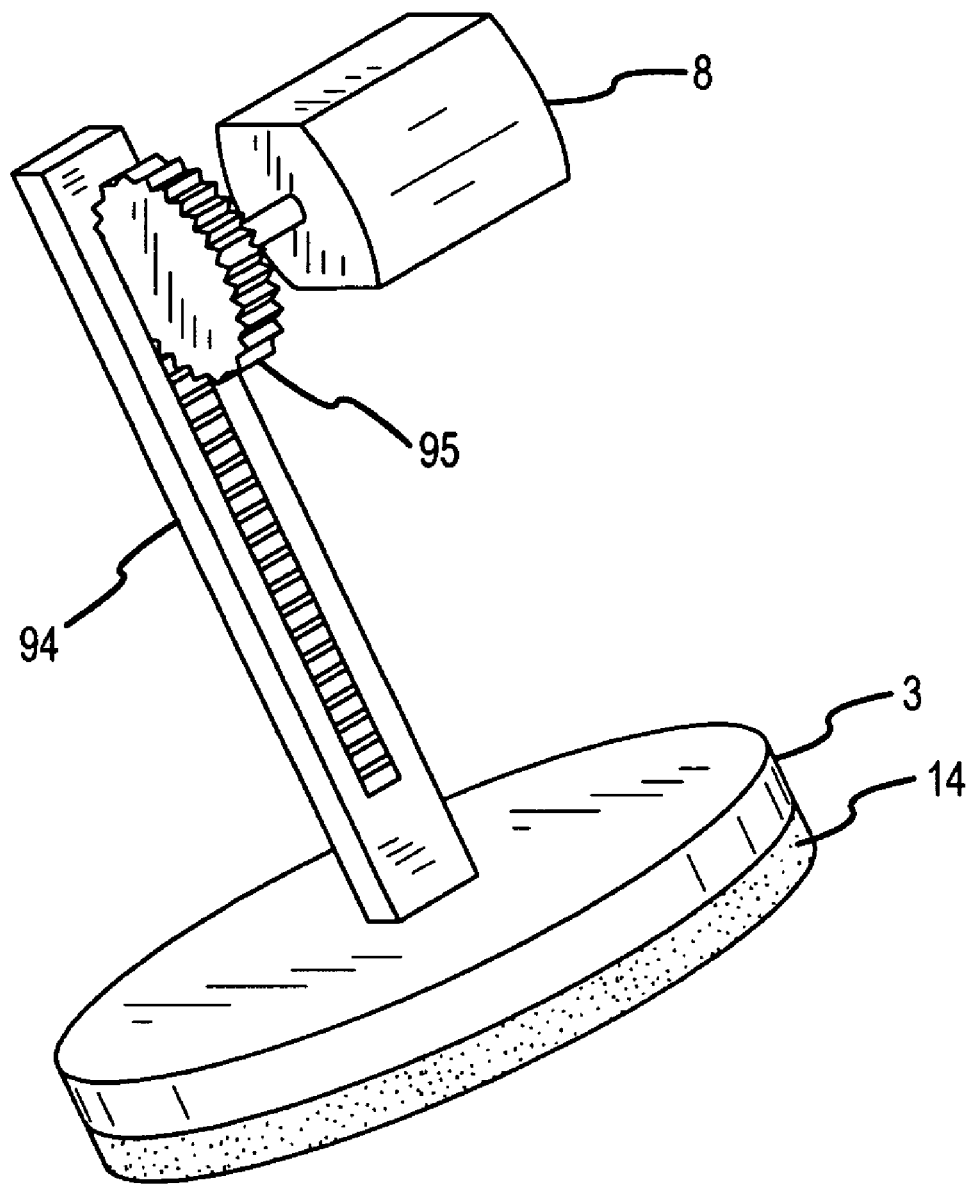
FIG. 9 shows another embodiment of the electrochemical means, the drive means and moveable piston of the vapor-dispersing device.

Referring now to FIG. 8, another embodiment of the drive means of the present invention is shown. In this configuration, the piston 3 and attached evaporative member 14 are moveable in a stroke path through the concerted motions possible from a hinged arm 92 movably fastened to the piston 3, and a rotating cam member 93 connected between the hinged arm 92 and the electromechanical means 8, which in this instance is preferably a simple motor. Similarly, as shown in FIG. 9, movement of the piston 3 and attached evaporative member 14 are possible along a defined stroke path by incorporation of a toothed gear 94 fixedly attached to piston 3, wherein the piston is moved in an up and down stroking fashion through the reversible rotation of gear 95 driven by motor 8. In this embodiment, the motor 8 would reverse direction by reversing the polarity of the voltage from the electrical means 10 to the motor 8.

The electrical control means 10 shown conceptually in FIGS. 1, 2, 3 and 7 may be of vast configurations depending on the power source desired for the device (AC or DC battery) and the level of independent control intended for the end user, for example if it further comprises logic control. Minimally the electrical control means 10 supplies power to the electromechanical means. It may house at least one battery within a battery compartment or it may conduct AC power from an electrical outlet through electrical receptacle prongs protruding directly from the housing of the device or from an electrical cord running from the device. For example, the control means 10 may comprise a voltage supply and a switch, with internal electrical connection to the electromechanical means. In this way the electrical control means 10 may take AC house current (110 or 220 v) and route it directly into the electromechanical means via wires and/or contacts. The main control switch may include a simple ON/OFF switch, and/or the electrical control means may also include a multiple position switch for "HIGH-MED-LOW" settings that provides for selection of three electrical current levels. The multiple-position switch may incorporate a rheostat to adjust the output of the device through adjustment of the frequency of the piston strokes, or may control an integrated circuit to control the strokes of the piston by adjusting the frequency, duration and polarity of the electrical signals to the electromechanical means. The control means 10 may be much more elaborate, comprising a timer circuit, an integrated circuit and/or a programmable integrated circuit. The electrical control means may further comprise a gas sensor for detecting malodors or marker molecules, or a light, motion or sound sensor, for example for turning on the power in the device when the device senses odors, marker molecules, light, movement and/or sounds. The electrical control means may further include a digital display for logic control. The programmable IC may allow the user to operate the device at different intensity levels. The function of the integrated circuit is to control the voltage signals to the electromechanical means. Incorporating a gas sensor, or light, motion or sound sensor may allow the device to operate independently of user interaction, (i.e., the device becomes entirely automatic).

FIG. 10 illustrates a preferred configuration of the reservoir for use in the present invention. In this preferred embodiment, the reservoir 6, the liquid transfer means 4 and a removable sealing member 27 become an article of manufacture 60 that may be merchandised as a refill for use in the device. In this way the user can change out reservoirs and keep the remainder of the device, including the relatively more expensive electronics, for reuse. As mentioned above, the user may also be able to remove and replace the evaporative member on the piston when changing out the reservoir. Various refills 60 may be marketed for use in the device of the present invention, for example many different fragrance varieties or different insecticidal refills for use against specific household and outdoor pests. As mentioned earlier, it is preferred to seal the reservoir 6 with a small sealing member such as a small cap 27 that fits snugly over the liquid transfer means 4 of the reservoir. This is particularly important if the liquid transfer means 4 is a fragile capillary tube (e.g. glass, fine diameter) rather than a fairly rigid wick, e.g. of porous plastic. In this particular embodiment illustrated, the cap 27 seals and protects the liquid transfer means 4 and the contents of the reservoir 6. Certainly there is no restriction to the size and shape of the sealing member 27, or the material of construction. Most preferred is to use a polypropylene injection molded plastic cap that snaps or screws over the liquid transfer means and at least part of the top surface of the reservoir. Alternatively the reservoir with volatile liquid 20 inside may be shrink-wrapped with plastic film, particularly if the liquid transfer means 4 is only protruding a small length from the reservoir. In this way, the consumer may purchase the described article of manufacture 60, pull off the sealing member 27 or peel away a foil seal or remove a shrink-wrapped film, and then insert the reservoir into the end of the housing where the liquid transfer means 4 will be placed in the path of the moving piston and corresponding evaporative member. Meanwhile the consumer may detach the previously used evaporative member from the piston and attach a replacement. Refill "kits" may be merchandised that provide both the new reservoir and new evaporative member in a single package. When the reservoir is emptied of the volatile liquid 20, the user may purchase a refill kit, pull out the empty reservoir, detach and replace the evaporative member, and then may press the new full reservoir back into the housing. Most preferred is to incorporate a viewing window on the housing of the device along with a clear or semi-transparent reservoir such that the consumer can easily see the level of volatile liquid remaining in the device and to know when to remove and replace the reservoir.

The volatile material 20 in the reservoir for evaporation from the device of the present invention may be present from about 0.1 gram to about 500 gram. Depending on whether the composition is a fragrance or an insecticide, the composition may contain anywhere from trace actives to 100% actives and may contain any number and amount of solvents and/or carriers, volatile or otherwise. For example, the device of the present invention may comprise a volatile material further consisting of only a single volatile chemical such as citronella. In another embodiment of the invention the volatile material may comprise only eucalyptus oil. The material may comprise anywhere from one or a few to up to many active materials dissolved or compounded with solvents and carriers that may or may not be volatile. Most preferred is to utilize volatile mixtures (comprising mixtures of actives and solvents together) wherein all of the components are volatile such that the reservoir will eventually be empty of any visible contents after use-up.

For use as a fragrancing device, the fragrance components of the volatile material in the present invention may comprise one of more volatile organic compounds available from any of the now known, or hereafter established, perfumery suppliers, such as International Flavors and Fragrances (IFF) of New Jersey, Givaudan of New Jersey, Firmenich of New Jersey, etc. Many types of fragrances can be used in the present invention. Preferably the fragrance materials are volatile essential oils. The fragrances, however, may be synthetically derived materials (aldehydes, ketones, esters, etc.), naturally derived oils, or mixtures thereof. Naturally derived fragrance substances include, but are not limited to, musk, civet, ambergis, castoreum and like animal perfumes; abies oil, ajowan oil, almond oil, ambrette seed absolute, angelic root oil, anise oil, basil oil, bay oil, benzoin resinoid, bergamot oil, birch oil, bois de rose oil, broom abs., cajeput oil, cananga oil, capsicum oil, caraway oil, cardamon oil, carrot seed oil, cassia oil, cedar leaf, cedarwood oil, celery seed oil, cinnamon bark oil, citronella oil, clary sage oil, clove oil, cognac oil, coriander oil, cubeb oil, cumin oil, camphor oil, dill oil, estragon oil, eucalyptus oil, fennel sweet oil, galbanum res., garlic oil, geranium oil, ginger oil, grapefruit oil, hop oil, hyacinth abs., jasmin abs., juniper berry oil, labdanum res., lavander oil, laurel leaf oil, lavender oil, lemon oil, lemongrass oil, lime oil, lovage oil, mace oil, mandarin oil, mimosa abs., myrrh abs., mustard oil, narcissus abs., neroli bigarade oil, nutmeg oil, oakmoss abs., olibanum res., onion oil, opoponax res., orange oil, orange flower oil, origanum, orris concrete, pepper oil, peppermint oil, peru balsam, petitgrain oil, pine needle oil, rose abs., rose oil, rosemary oil, sandalwood oil, sage oil, spearmint oil, styrax oil, thyme oil, tolu balsam, tonka beans abs., tuberose abs., turpentine oil, vanilla beans abs., vetiver oil, violet leaf abs., ylang ylang oil and like vegetable oils, etc. Synthetic fragrance materials include but are not limited to pinene, limonene and like hydrocarbons; 3,3,5-trimethylcyclohexanol, linalool, geraniol, nerol, citronellol, menthol, borneol, borneyl methoxy cyclohexanol, benzyl alcohol, anise alcohol, cinnamyl alcohol, β-phenyl ethyl alcohol, cis-3-hexenol, terpineol and like alcohols; anethole, musk xylol, isoeugenol, methyl eugenol and like phenols; α-amylcinnamic aldehyde, anisaldehyde, n-butyl aldehyde, cumin aldehyde, cyclamen aldehyde, decanal, isobutyl aldehyde, hexyl aldehyde, heptyl aldehyde, n-nonyl aldehyde, nonadienol, citral, citronellal, hydroxycitronellal, benzaldehyde, methyl nonyl acetaldehyde, cinnamic aldehyde, dodecanol, α-hyxylcinnamic aldehyde, undecenal, heliotropin, vanillin, ethyl vanillin and like aldehydes; methyl amyl ketone, methyl β-naphthyl ketone, methyl nonyl ketone, musk ketone, diacetyl, acetyl propionyl, acetyl butyryl, carvone, menthone, camphor, acetophenone, p-methyl acetophenone, ionone, methyl ionone and like ketones; amyl butyrolactone, diphenyl oxide, methyl phenyl glycidate, .gamma.-nonyl lactone, coumarin, cineole, ethyl methyl phenyl glicydate and like lactones or oxides; methyl formate, isopropyl formate, linalyl formate, ethyl acetate, octyl acetate, methyl acetate, benzyl acetate, cinnamyl acetate, butyl propionate, isoamyl acetate, isopropyl isobutyrate, geranyl isovalerate, allyl capronate, butyl heptylate, octyl caprylate octyl, methyl heptynecarboxylate, methine octynecarboxylate, isoacyl caprylate, methyl laurate, ethyl myristate, methyl myristate, ethyl benzoate, benzyl benzoate, methylcarbinylphenyl acetate, isobutyl phenylacetate, methyl cinnamate, cinnamyl cinnamate, methyl salicylate, ethyl anisate, methyl anthranilate, ethyl pyruvate, ethyl α-butyl butylate, benzyl propionate, butyl acetate, butyl butyrate, p-tert-butylcyclohexyl acetate, cedryl acetate, citronellyl acetate, citronellyl formate, p-cresyl acetate, ethyl butyrate, ethyl caproate, ethyl cinnamate, ethyl phenylacetate, ethylene brassylate, geranyl acetate, geranyl formate, isoamyl salicylate, isoamyl isovalerate, isobornyl acetate, linalyl acetate, methyl anthranilate, methyl dihydrojasmonate, nopyl acetate, β-phenylethyl acetate, trichloromethylphenyl carbinyl acetate, terpinyl acetate, vetiveryl acetate and like esters, and the like. Suitable fragrance mixtures may produce a number of overall fragrance type perceptions including but not limited to, fruity, musk, floral, herbaceous (including mint), and woody, or perceptions that are in-between (fruity-floral for example). Typically these fragrance mixtures are compounded by mixing a variety of these active fragrance materials along with various solvents to adjust cost, evaporation rates, hedonics and intensity of perception. Well known in the fragrance industry is to dilute essential fragrance oil blends (natural and/or synthetic) with solvents such as ethanol, isopropanol, hydrocarbons, acetone, glycols, glycol ethers, water, and combinations thereof, and using solvent up to as much as 90% of the volatile fragrance composition. Thus a preferred fragrance composition for use as the volatile composition in the present invention is comprised of a mixture of many fragrance actives and volatile solvents, sometimes along with smaller amounts of emulsifiers, stabilizers, wetting agents and preservatives. More often than not, the compositions of the fragrance mixtures purchasable from the various fragrance supply houses remain proprietary.

Volatile insecticide compositions for use in the present invention are those of the type described in U.S. Pat. No. 4,663,315 (to Hasegawa, et al.) and incorporated herein by reference. Hasegawa describes many useful volatile insecticidal compositions that will work well within the reservoir of the present invention.

The volatile material for use in the present invention has been described as a liquid, however it is important to realize that any range of viscosities may be used for this liquid depending on the configuration and length of the liquid transfer means. For example, the material placed into the reservoir for evaporation may be a "water-thin" liquid, a thickened gel, an emulsion or suspension, or a moderate to very viscous liquid, for example resembling a gel or a waxy semi-solid. Using a volatile liquid with substantially high viscosity has the advantage that the device may be held and operated in a variety of positions (even upside-down) without fear of leaking or dripping from the liquid transfer means.

Each time the evaporative member contacts the exposed end of the liquid transfer means a small amount of volatile liquid is wicked into the evaporative member by capillary action. In one preferred configuration described above the liquid transfer means is a simple capillary tube in communication with the volatile liquid. The first end of the liquid transfer means is inserted into the reservoir and is in communication with the volatile liquid and the second end of the liquid transfer means is protruding at least somewhat from the reservoir and is exposed. In that configuration, the evaporative member contacts the end of the capillary tube at the extreme end of the piston stroke and during that brief contact transfers a small amount of liquid out from the capillary tube onto the evaporative means. Liquid from the reservoir then quickly refills the depleted capillary tube. The liquid on the evaporative member then evaporates into the surrounding environment, assisted by the motion of the piston and the wafting of air. The frequency of the piston stroking will determine the frequency of liquid pick-up at the end of the liquid transfer means (the frequency of contact between the evaporative member and the liquid transfer means) and the degree to which the air is moved and the material evaporated from the evaporative member. In the ideal configuration, the evaporative member is never completely saturated. The piston strokes may also be configured such that there is a short pause at each end of the stroke length. For example, wherein the piston comes into contact with the liquid transfer means, resting momentarily to pick up liquid, then to move away in the opposite direction.

We have herein described a unique and heretofore unknown vapor-dispensing device and vapor-dispersing method that comprises a moving piston in the absence of heating elements or building pressure. The device operates at ambient temperature and pressure and evaporates the contents of a reservoir through the repeated touching of an evaporative member to a liquid transfer means in communication with the material to be evaporated. The moving piston provides for air movement to assist in moving the vapors out from the unit and may also provide a noise such as a clicking sound to indicate to the consumer that the unit is operating. This invention will find use as an air freshener and an insecticidal device.

We claim:

1. A vapor-dispersing device comprising:
   a. a housing with top, bottom, side walls and an interior;
   b. a vent on said housing allowing air flow between said interior and the environment exterior to said housing;
   c. a piston moveable along a path between first and second positions within said housing, said piston comprising a top, bottom and sidewalls;
   d. a substantially flat evaporative pad member attached against the bottom of said piston;
   e. a reservoir positioned within said housing having an opening;
   f. a volatile liquid contained within said reservoir;
   g. a liquid transfer means with a first end positioned in said opening and in communication with said volatile liquid, and a second end protruding from said reservoir;
   h. a drive means connected to said piston opposite said evaporative pad member for repetitively touching said pad onto said second end of said liquid transfer means;
   i. an electromechanical means connected to said drive means for electromechanically moving said piston along said path within said housing through said drive means; and,
   j. an electrical control means for powering and electronically controlling said electromechanical means.

2. The vapor-dispersing device of claim 1, wherein said evaporative pad member is selected from the group consisting of cellulose, cotton, synthetic fibers and fiberboard.

3. The vapor-dispersing device of claim 1, wherein said liquid transfer means is a porous plastic or graphite wick.

4. The vapor-dispersing device of claim 1, wherein said opening is fitted with a fitment to seal said liquid transfer means within said opening.

5. The vapor-dispersing device of claim 1, wherein said liquid transfer means is a glass or plastic capillary tube.

6. The vapor-dispersing device of claim 1, wherein said second end of said liquid transfer means is initially sealed closed with a removable sealing member chosen from the group consisting of foil film, plastic film and a plastic cap.

7. The vapor-dispersing device of claim 1, wherein said electromechanical means is an AC or DC electrical motor.

8. The vapor dispersing device of claim 7, wherein said drive means further comprises at least one toothed gear.

9. The vapor dispersing device of claim 7, wherein said drive means further comprises a hinged arm and rotating cam connected between said motor and said piston.

10. The vapor-dispersing device of claim 1, wherein said electromechanical means is selected from the group consisting of a push-type solenoid, pull-type solenoid, and a push/pull-type solenoid.

11. The vapor-dispersing device of claim 10, wherein said drive means consists of a metal pin surrounded by a spring attached to the top of said piston.

12. The vapor dispersing device of claim 1, wherein said electrical control means further includes an electrical cord terminating in a plug having suitable prong configuration for connection to a 110 volt or 220 volt electrical outlet.

13. The vapor dispersing device of claim 1, wherein said electrical control means further includes electrical prongs protruding directly from said housing for plugging said device directly into a 120 volt or 220 volt electrical outlet for both support and electrical power.

14. The vapor dispersing device of claim 1, wherein said electrical control means further comprises a rectifier.

15. The vapor dispersing device of claim 1, wherein said electrical means further comprises at least one battery and a moveable door for accessing said battery.

16. The vapor dispersing device of claim 1, wherein said electrical means further comprises an ON/OFF switch.

17. The vapor dispersing device of claim 1, wherein said electrical means further comprises a timer circuit programmable by the user.

18. The vapor dispersing device of claim 1, wherein said electrical control means further comprises a logic circuit for programming run time and intensity output of the device.

19. The vapor-dispersing device of claim 1, wherein said volatile liquid is a blend of synthetic or natural fragrance oils and solvents.

20. The vapor-dispersing device of claim 1, wherein said volatile liquid is an insecticide mixture.

21. A method for dispensing vapor into the environment comprising the steps of:
   a. providing a vapor-dispersing device according to claim 1; and,
   b. interacting with said electrical control means to operate said device.

* * * * *